United States Patent
Fu

(12) 
(10) Patent No.: US 6,503,899 B2
(45) Date of Patent: Jan. 7, 2003

(54) AZEPINO[4,5-B]PYRANO[3,2-E]INDOLES

(75) Inventor: Jian-min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/900,508

(22) Filed: Jul. 6, 2001

(65) Prior Publication Data

US 2002/0022616 A1 Feb. 21, 2002

Related U.S. Application Data

(63) Continuation-in-part of application No. PCT/US01/18777, filed on Jun. 8, 2001.
(60) Provisional application No. 60/216,286, filed on Jul. 6, 2000.

(51) Int. Cl.[7] ................... A61K 31/55; C07D 491/12; A61P 25/00
(52) U.S. Cl. ........................ 514/215; 540/578
(58) Field of Search ........................ 514/215; 540/578

(56) References Cited

U.S. PATENT DOCUMENTS

| | | | |
|---|---|---|---|
| 3,553,232 A | 1/1971 | Hester, Jr. | 260/326.5 |
| 3,622,673 A | 11/1971 | Hester, Jr. | 424/274 |
| 3,652,588 A | 3/1972 | Hester, Jr. | 260/326.3 |
| 3,676,558 A | 7/1972 | Hester, Jr. | 424/274 |
| 3,776,922 A | 12/1973 | Epstein et al. | 260/326.5 B |
| 3,839,357 A | 10/1974 | Hester, Jr. | 260/326.5 B |

FOREIGN PATENT DOCUMENTS

| | | |
|---|---|---|
| EP | 0028381 | 5/1981 |
| FR | 6699 | 2/1969 |
| WO | WO00/64899 | 11/2000 |

OTHER PUBLICATIONS

Hester, J.B., et al., "Azepinooidoles. I. Hexahydroazepinol (4,5–b) indoles", *J. Med. Chem*, 11, No. 1, 101–106, (1968).

Kelley, J.M., et al., "Comparison of common interatomic distances in serotonin and some hallucinogenic drugs", *Database accession No. 80:33702, Pharmacology 10(1),* 28–31, (1973).

Mash, D.C., et al., "Identification of a primary metabolite of ibogaine that targets serotonin transporters and elevates serotonin", *Database accession No. 123:47718 Life Sci.,* 57(3), PL45–PL50, (1995).

Sweetnam, P.M., et al., "Receptor binding profile suggests multiple mechanisms of action are responsiblefor ibogaine's putative anti–addictive activity", *Chemical Abstracts Service, Columbus, OH, Psychopharmacology (Berlin)* 118(4), 369–76, (1995).

*Primary Examiner*—Brenda Coleman
(74) *Attorney, Agent, or Firm*—Schwegman, Lundberg, Woessner & Kluth, P.A.

(57) ABSTRACT

The invention provides a compound of formula (I):

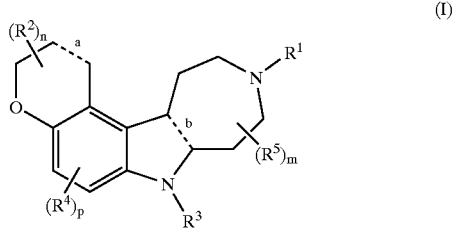

wherein: $R^1$–$R^5$, m, n, p, and the bonds a and b represented by - - - have any of the values, specific values, or preferred values described in the specification; or a salt or solvate thereof. The invention also provides pharmaceutical compositions comprising such a compound, as well as intermediates and processes useful for preparing such a compound, and therapeutic methods including the administration of such a compound.

33 Claims, No Drawings

AZEPINO[4,5-B]PYRANO[3,2-E]INDOLES

This application is a continuation-in-part of International Patent Application Number PCT/US01/18777, filed Jun. 8, 2001, and also claims priority under 35 U.S.C. §119(e) from U.S. Provisional Application No. 60/216,286, filed Jul. 6, 2000.

FIELD OF THE INVENTION

The present invention generally relates to a series of compounds, to pharmaceutical compositions containing the compounds, and to uses of the compounds and compositions as therapeutic agents. More specifically, compounds of the present invention are pyranoazepinoindole compounds, which are serotonin receptor (5-HT) ligands and are useful for treating diseases, disorders, and conditions wherein modulation of the activity of serotonin receptors (5-HT) is desired.

BACKGROUND

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, a heightened interest exists for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors (5-HT$_{1-7}$) contain fourteen to eighteen separate receptors that have been formally classified. See Glennon, et al., *Neuroscience and Behavioral Reviews*, 1990, 14, 35; and D. Hoyer, et al. *Pharmacol. Rev.* 1994, 46, 157–203.

For example, the 5-HT$_2$ family of receptors contains 5-HT$_{2A}$, 5-HT$_{2B}$, and 5-HT$_{2C}$ subtypes, which have been grouped together on the basis of primary structure, secondary messenger system, and operational profile. All three 5-HT$_2$ subtypes are G-protein coupled, activate phospholipase C as a principal transduction mechanism, and contain a seven-transmembrane domain structure. There are distinct differences in the distribution of the three 5-HT$_2$ subtypes in a mammal. The 5-HT$_{2B}$ and 5-HT$_{2A}$ receptors are widely distributed in the peripheral nervous system, while the 5-HT$_{2C}$ receptor has been found only in the central nervous system, being highly expressed in many regions of the human brain. See G. Baxter, et al. *Trends in Pharmacol. Sci.* 1995, 16, 105–110.

Subtype 5-HT$_{2A}$ has been associated with effects including vasoconstriction, platelet aggregation, and bronchoconstriction, while subtype 5-HT$_{2C}$ has been associated with diseases that include depression, anxiety, obsessive compulsive disorder, panic disorders, phobias, psychiatric syndromes, and obesity. Very little is known about the pharmocologic role of the 5-HT$_{2B}$ receptor. See F. Jenck, et al., *Exp. Opin. Invest. Drugs*, 1998, 7,1587–1599; M. Bos, et al., *J. Med. Chem.*, 1997, 40, 2762–2769; J. R. Martin, et al., *The Journal of Pharmacology and Experimental Therapeutics*, 1998, 286, 913–924; S. M. Bromidge, et al., *J. Med. Chem.*, 1998, 41,1598–1612; G. A. Kennett, *Drugs*, 1998, 1, 4, 456–470; and A. Dekeyne, et al., *Neuropharmacology*, 1999, 38, 415–423.

U.S. Pat. Nos. 3,553,232 and 3,622,673 disclose 4-(1,4,5,6-tetrahydroazepine[4,5-b]indole-3(2H)-yl) butyrophenones, which are reported to be useful in the treatment of mental or emotional disorders.

U.S. Pat. Nos. 3,652,588, 3,676,558, and 3,839,357 disclose 6-alkyl-1,2,3,4,5,6-hexahydroazepino[4,5-b]indoles and aneroxigenic compounds thereof that are reported to be useful to tranquilize and otherwise sedate mammals or to suppress hunger in mammals.

In spite of the above-cited publications, there remains a need for pharmaceutical agents that are useful in treating a variety of diseases, disorders, and conditions that are associated with serotonin (5-HT) receptors.

SUMMARY OF THE INVENTION

Generally, the present invention is directed to methods and compositions useful in treating a disease, disorder, and/or condition in a mammal wherein a 5-HT receptor is implicated, and modulation of a 5-HT function is desired, by using a novel compound disclosed herein.

In accordance with the present invention, novel compounds that demonstrate useful biological activity, and particularly activity as 5-HT receptor ligands, are provided. More specifically, the invention provides a compound of formula (I):

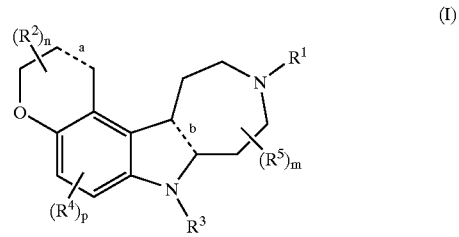

wherein:

R$^1$ is selected from the group consisting of H, C$_{1-8}$alkyl and C$_{1-8}$alkylenearyl;

each R$^2$, independently, is selected from the group consisting of halo, C$_{1-8}$alkyl, C$_{1-8}$alkoxy, aryl, and OH;

R$^3$ is selected from the group consisting of hydrogen, C$_{1-8}$alkyl, aryl, heteroaryl, C(=O)R$^a$, C(=O)OR$^a$, C(=O)NR$^a$R$^b$, C(=O)SR$^a$, C(=S)NR$^a$R$^b$, SO$_2$R$^a$, SO$_2$NR$^a$R$^b$, S(=O)R$^a$, S(=O)NR$^a$R$^b$, C(=O)NR$^a$C$_{1-6}$ alkyleneOR$^a$, C(=O)NR$^a$C$_{1-6}$alkyleneHet, C(=O)C$_{1-6}$alkylenearyl, C(=O)C$_{1-6}$alkyleneheteroaryl, C$_{1-6}$alkylenearyl, C$_{1-6}$alkyleneheteroaryl, C$_{1-6}$alkyleneHet, C$_{1-6}$alkyleneC(=O)C$_{1-6}$ alkylenearyl, C$_{1-6}$alkyleneC(=O)C$_{1-6}$ lkyleneheteroaryl, C$_{1-6}$alkyleneC(=O)Het, C$_{1-6}$alkyleneC(=O)NR$^a$R$^b$, C$_{1-6}$alkyleneOR$^a$, C$_{1-6}$alkyleneNR$^a$C(=O)R$^a$, C$_{1-6}$alkyleneOC$_{1-6}$alkyleneOR$^a$, C$_{1-6}$alkyleneNR$^a$R$^b$, C$_{1-6}$alkyleneC(=O)OR$^a$, C$_{1-6}$alkyleneOC$_{1-6}$alkyleneC(=O)OR$^a$, C$_{1-6}$alkyleneC(=O)aryl, C$_{1-6}$alkyleneC(=O)heteroaryl, C$_{1-6}$alkyleneOC$_{1-6}$alkylenearyl, C$_{1-6}$alkyleneOC$_{1-6}$alkyleneheteroaryl, $C_{1-6}$alkyleneOC$_{1-6}$alkyleneHet, $C_{1-6}$alkyleneSR$^a$, $C_{1-6}$alkyleneSO$_2$R$^a$, $C_{1-6}$alkyleneS(=O)R$^a$; $C_{1-6}$alkyleneSO$_2$NR$^a$R$^b$, and $C_{1-6}$alkyleneNSO$_2$R$^a$;

each R$^4$, independently, is selected from the group consisting of halo, OH, CN, NO$_2$, CF$_3$, CF$_3$O, NR$^a$R$^b$, $C_{1-8}$alkyl, $C_{1-8}$alkoxy, $C_{1-8}$alkanoyl, $C_{1-8}$alkoxycarbonyl, $C_{1-8}$alkanoyloxy, aryl, heteroaryl, $C_{1-6}$alkylenearyl, and $C_{1-6}$alkyleneheteroaryl;

each R$^5$, independently, is selected from the group consisting of halo, $C_{1-8}$alkyl, $C_{1-8}$alkoxy, and OH;

m is 0, 1, 2, 3, 4, 5, 6, 7, or 8;

n is 0, 1, 2, 3, 4, 5, or 6;

p is 0, 1, or 2;

bond a and bond b represented by - - - are each independently a single bond or a double bond;

R$^a$ and R$^b$, independently, are selected from the group consisting of hydrogen, $C_{1-8}$alkyl, aryl, heteroaryl, arylC$_{1-3}$alkyl, heteroarylC$_{1-3}$alkyl, $C_{1-3}$alkylenearyl, $C_{1-3}$alkyleneheteroaryl, and Het;

or a pharmaceutically acceptable salt or solvate thereof.

Another embodiment of the present invention provides a pharmaceutical composition comprising a compound of Formula (I), or a pharmaceutically acceptable salt or solvate thereof, and a pharmaceutically acceptable carrier.

Still another embodiment of the present invention provides a method of treating a disease, disorder, and/or condition in a mammal (e.g., animal or human), wherein a 5-HT receptor is implicated and modulation of a 5-HT function is desired. The method comprises administering a therapeutically effective amount of a compound of Formula (I), or a pharmaceutically acceptable salt or solvate thereof, to the mammal.

Yet another embodiment of the present invention comprises a method of modulating 5-HT receptor function comprising contacting the receptor with an effective amount of a compound of Formula (I), or a pharmaceutically acceptable salt or solvate thereof.

A further embodiment of the present invention provides a method of treating or preventing diseases, disorders, and/or conditions of the central nervous system in a mammal, comprising administering a therapeutically effective amount of a compound of Formula (I), or a pharmaceutically acceptable salt or solvate thereof, to the mammal.

Specific diseases, disorders, and/or conditions for which the compound of Formula (I) has activity include, but are not limited to, obesity, depression, schizophrenia, schizophreniform disorder, schizoaffective disorder, delusional disorder, a stress related disease (e.g., general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g., a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition, e.g., dementia, mental retardation or delirium), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders and psychotic disorder due to medical condition), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome).

Yet another embodiment of the present invention comprises a compound of Formula (I), or a pharmaceutically acceptable salt or solvate thereof, for use in medical therapy or diagnosis.

Yet another embodiment of the present invention comprises the use of a compound of Formula (I), or a pharmaceutically acceptable salt or solvate thereof, in the preparation of a medicament for treating or preventing diseases, disorders, and conditions of the central nervous system.

The invention also provides synthetic intermediates and processes disclosed herein, which are useful for preparing compounds of formula (I).

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION

In describing the preferred embodiments, certain terminology has been utilized for the sake of clarity. Such terminology is intended to encompass the recited embodiments as well as all technical equivalents which operate in a similar manner for a similar purpose to achieve a similar result.

The following definitions are used, unless otherwise described:

The term "alkyl" includes straight chained and branched hydrocarbon groups containing the indicated number of carbon atoms, typically methyl, ethyl, and straight chain and branched propyl, and butyl groups. The term "alkyl" also encompasses cycloalkyl, i.e., a cyclic $C_3$–$C_8$ hydrocarbon group such as, for example, cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkoxy" is defined as —OR, wherein R is alkyl.

The term "halo" is defined herein to include fluoro, chloro, bromo, and iodo. Similarly, the term "halogen" is defined herein to include fluorine, chlorine, bromine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," is defined herein as a monocyclic or bicyclic aromatic group (e.g., phenyl or naphthyl) that can be unsubstituted or substituted, for example, with one or more, and in particular one to three of the following substituents selected from the group consisting of H, halo, CN, NO$_2$, CF$_3$, N$_3$, C$_{1-6}$alkyl, OH, NR$^a$R$^b$, OR$^a$, C(=O)NR$^a$R$^b$, C(=S)NR$^a$R$^b$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl. Generally, the term "heteroaryl" denotes a monocyclic or polycyclic aromatic ring containing five or six ring atoms containing carbon and 1, 2, 3, or 4 heteroatoms independently selected from the group consisting of non-peroxide oxygen, sulfur, and N(Z) wherein Z is absent or is H, O, C$_{1-4}$alkyl, phenyl or benzyl.

The term "Het" generally represents a heterocyclic group, saturated or partially unsaturated, containing at least one heteroatom selected from the group consisting of oxygen, nitrogen, and sulfur, and optionally substituted with C$_{1-6}$alkyl or C(=O)OR$^b$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, a pyrroline, 2H-pyran, 4H-pyran, morpholine, thiomorpholine, piperidine, 1,4-dithiane, and 1,4-dioxane.

The term "alkylene" refers to an alkyl group having a substituent. For example, the term "C$_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "amino" is defined as —NH$_2$, and the term "alkylamino" is defined as —NR$_2$, wherein at least one R is alkyl and the second R is alkyl or hydrogen. The term "acylamino" is defined as RC(=O)N, wherein R is alkyl or aryl.

The carbon atom content of various hydrocarbon-containing moieties is indicated by a prefix designating the minimum and maximum number of carbon atoms in the moiety, i.e., the prefix C$_{i-j}$ indicates a moiety of the integer "i" to the integer "j" carbon atoms, inclusive. Thus, for example, "C$_{1-6}$ alkyl" refers to alkyls having one to six carbon atoms, inclusive.

Abbreviations which are well known to one of ordinary skill in the art also are used, e.g., "Bz" for benzoyl, "Bn" for benzyl, and "Ph" for phenyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine serotonin receptor binding properties and activity using the standard tests described herein, or using other similar tests which are well known in the art.

Specific and preferred values listed below for groups or moieties, substituents, and ranges, are for purposes of illustration only and do not exclude other defined values or other values within the defined ranges.

Specifically, C$_{1-8}$alkyl can be methyl, ethyl, propyl, isopropyl, butyl, iso-butyl, sec-butyl, pentyl, 3-pentyl, hexyl, heptyl, octyl, cyclopropyl, cyclobutyl, cyclopentyl, cyclohexyl, cycloheptyl, cyclooctyl, or cyclopropylmethyl; C$_{1-6}$alkylene can be methylene, ethylene, propylene, isopropylene, butylene, iso-butylene, sec-butylene, pentylene, or hexylene; C$_{1-8}$alkoxy can be methoxy, ethoxy, propoxy, isopropoxy, butoxy, iso-butoxy, sec-butoxy, pentoxy, 3-pentoxy, hexyloxy, heptyloxy, or octyloxy; C$_{1-8}$alkanoyl can be acetyl, propanoyl or butanoyl; C$_{1-8}$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; C$_{1-8}$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, R$^1$ is selected from the group consisting of hydrogen and benzyl.

Specifically, each R$^2$, independently, is selected from the group consisting of C$_{1-8}$alkyl and OH.

Specifically, R$^2$ is phenyl.

Specifically, each R$^2$, independently, is selected from the group consisting of halo, C$_{1-8}$alkoxy, and OH.

Specifically, R$^3$ is selected from the group consisting of hydrogen, C$_{1-6}$alkyleneOR$^a$, C$_{1-6}$alkyleneC(=O)OR$^a$, C$_{1-6}$alkyleneC(=O)NR$^a$R$^b$.

Specifically, R$^3$ is selected from the group consisting of hydrogen, C$_{1-8}$alkyl, aryl, heteroaryl, C(=O)R$^a$, C(=O)OR$^a$, C(=O)NR$^a$R$^b$, C(=O)SR$^a$, C(=S)NR$^a$R$^b$, SO$_2$R$^a$, SO$_2$NR$^a$R$^b$, S(=O) R$^a$, S(=O)NR$^a$R$^b$, C$_{1-6}$alkylenearyl, C$_{1-6}$alkyleneheteroaryl, C$_{1-6}$alkyleneHet, C$_{1-6}$alkyleneC(=O)NR$^a$ R$^b$, C$_{1-6}$alkyleneOR$^a$, C$_{1-6}$alkyleneNR$^a$C(=O)R$^a$, C$_{1-6}$alkyleneNR$^a$R$^b$, C$_{1-6}$alkyleneC(=O)OR$^a$, C$_{1-6}$alkyleneC(=O)Het, C$_{1-6}$alkyleneC(=O)aryl, C$_{1-6}$alkyleneC(=O)heteroaryl, C$_{1-6}$alkyleneOC$_{1-6}$alkylenearyl, C$_{1-6}$alkyleneOC$_{1-6}$alkyleneheteroaryl, C$_{1-6}$alkyleneOC$_{1-6}$alkyleneHet, C$_{1-6}$alkyleneSR$^a$, C$_{1-6}$alkyleneSO$_2$R$^a$, C$_{1-6}$alkyleneS(=O)R$^a$; C$_{1-6}$alkyleneSO$_2$NR$^a$R$^b$, and C$_{1-6}$alkyleneNSO$_2$R$^a$.

Specifically, R$^3$ is selected from the group consisting of hydrogen, C$_{1-8}$alkyl, aryl, heteroaryl, SO$_2$R$^a$, C$_{1-6}$alkylenearyl, C$_{1-6}$alkyleneheteroaryl, C$_{1-6}$alkyleneHet, C$_{1-6}$alkyleneC(=O)C$_{1-6}$alkylenearyl, C$_{1-6}$alkyleneC(=O)C$_{1-6}$alkyleneheteroaryl, C$_{1-6}$alkyleneC(=O)Het, C$_{1-6}$alkyleneC(=O)NR$^a$R$^b$, C$_{1-6}$alkyleneOR$^a$, C$_{1-6}$alkyleneNR$^a$C(=O)R$^a$, C$_{1-6}$alkyleneOC$_{1-6}$alkyleneOR$^a$, C$_{1-6}$alkyleneNR$^a$R$^b$, C$_{1-6}$alkyleneC(=O)OR$^a$, and C$_{1-6}$alkyleneOC$_{1-6}$alkyleneC(=O)OR$^a$.

Specifically, $R^3$ is hydrogen, methyl, 4-phenoxybutyl, carboxymethyl (—$CH_2COOH$), or N-phenylacetamide (PhNHC(=O)$CH_2$—).

Specifically, each $R^4$, independently, is halo, OH, CN, $NO_2$, $CF_3$, $CF_3O$, $NR^aR^b$, aryl, or heteroaryl.

Specifically, each $R^4$, independently, is halo, OH, CN, $NO_2$, $CF_3$, $CF_3O$, $NR^aR^b$, $C_{1-8}$alkyl, $C_{1-8}$alkoxy, $C_{1-8}$alkanoyl, $C_{1-8}$alkoxycarbonyl, or $C_{1-8}$alkanoyloxy.

Specifically, each $R^5$, independently, is selected from the group consisting of $C_{1-8}$alkyl and OH.

Specifically, each $R^5$, independently, is selected from the group consisting of halo, $C_{1-8}$alkoxy, and OH.

Specifically, m is 1 or 2.

Specifically, n is 0.

Specifically, n is 1 or 2.

Specifically, p is 0 or 1.

Specifically, p is 1 or 2.

A specific group of compounds are compounds wherein $R^2$ and $R^4$ are hydrogen; and $R^3$ is selected from the group consisting of hydrogen, alkyl, $C_{1-6}$alkylenearyl, $C_{1-6}$alkyleneOR$^a$, carboxylic acid, $C_{1-6}$alkyleneC(=O)OR$^a$, and $C_{1-6}$alkyleneC(=O)NR$^a$R$^b$.

A preferred compound of formula (1) is a compound of formula (IV):

(IV)

wherein:

$R^1$ is selected from the group consisting of H; $C_{1-6}$alkyl, and $C_{1-6}$alkylenearyl;

$R^2$ is selected from the group consisting of H, $C_{1-4}$alkyl, and OH;

$R^3$ is selected from the group consisting of hydrogen, alkyl, aryl, heteroaryl, C(=O)R$^a$, C(=O)OR$^a$, C(=O)NR$^a$R$^b$, C(=O)SR$^a$, C(=S)NR$^a$R$^b$, $SO_2$R$^a$, $SO_2$NR$^a$R$^b$, S(=O)R$^a$, S(=O)NR$^a$R$^b$, C(=O)NR$^a$C$_{1-6}$ alkyleneneOR$^a$, C(=O)NR$^a$C$_{1-6}$alkyleneHet, C(=O)C$_{1-6}$alkylenearyl, C(=O)C$_{1-6}$alkyleneheteroaryl, C$_{1-6}$alkylenearyl, C$_{1-6}$alkyleneheteroaryl, C$_{1-6}$alkyleneHet, C$_{1-6}$alkyleneC(=O)C$_{1-6}$alkylenearyl, C$_{1-6}$alkyleneC(=O)C$_{1-6}$alkyleneheteroaryl, C$_{1-16}$alkyleneC(=O)Het, C$_{1-6}$alkyleneC(=O)NR$^a$R$^b$, C$_{1-6}$alkyleneOR$^a$, C$_{1-6}$alkyleneNR$^a$C(=O)R$^a$, C$_{1-6}$alkyleneOC$_{1-6}$alkyleneOR$^a$, C$_{1-6}$alkyleneNR$^a$R$^b$, C$_{1-6}$alkyleneC(=O)OR$^a$, and C$_{1-6}$alkyleneOC$_{1-6}$alkyleneC(=O)OR$^a$, $R^4$ is selected from the group consisting of H, halo, OH, CN, $NO_2$, $CF_3$, $CF_3O$, $NR^aR^b$, aryl, and heteroaryl;

$R^5$ is selected from the group consisting of H, $C_{1-4}$alkyl, and OH; and $R^a$ and $R^b$, independently, are selected from the group consisting of hydrogen, $C_{1-6}$alkyl, $C_{3-8}$cycloalkyl, aryl, heteroaryl, arylC$_{1-3}$alkyl, heteroarylC$_{1-3}$alkyl, C$_{1-3}$alkylenearyl, C$_{1-3}$alkyleneheteroaryl, and Het;

or a pharmaceutically acceptable salt thereof.

For a compound of formula (I–IV), preferably, $R^3$ is selected from the group consisting of hydrogen; $C_{1-8}$alkyl, C$_{1-6}$alkyleneOR$^a$, C$_{1-6}$alkyleneC(=O)OR C$_{1-6}$alkyleneC(=O)NR$^a$R$^b$, C(=O)R$^a$, C(=S)NR$^a$R$^b$, and C(=O)C$_{1-6}$ alkylenearyl.

For a compound of formula (I–IV), preferably, $R^1$ is selected from the group consisting of hydrogen and benzyl.

For a compound of formula (I–IV), preferably, $R^2$ and $R^4$ are hydrogen.

For a compound of formula (I–IV), preferably, $R^3$ is selected from the group consisting of hydrogen, $C_{1-8}$alkyl, C$_{1-6}$alkylenearyl, C$_{1-6}$alkyleneOR$^a$, carboxylic acid, C$_{1-6}$alkyleneC(=O)OR$^a$, and C$_{1-6}$alkyleneC(=O)NR$^a$R$^b$.

For a compound of formula (I–IV), preferably, $R^3$ is selected from the group consisting of hydrogen, methyl, C$_4$alkylene-O-phenyl, —$CH_2$COOEt, —$CH_2$COOH, and N-phenylacetamide.

A preferred compound of the invention is:

(1) 10-benzyl-7,8,9,10,11,12-hexahydro-3H-azepino[4,5-b]pyrano[3,2-e]indole;

(2) 10-benzyl-7-methyl-7,8,9,10,11,12-hexahydro-3H-azepino[4,5-b]pyrano[3,2-e]indole;

(3) 2,3,7,8,9,10,11,12-octahydro-1H-azepino[4,5-b]pyrano[3,2-e]indole;

(4) 2,3,7,8,9,10,11,12-octahydro-7-methyl-1H-azepino[4,5-b]pyrano[3,2-e]indole;

(5) 10-benzyl-7-(4-phenoxybutyl)-7,8,9,10,11,12-hexahydro-3H-azepino[4,5-b]pyrano[3,2-e]indole;

(6) 7-(4-phenoxybutyl)-7,8,9,10,11,12-octahydro-1H-azepino[4,5-b]pyrano[3,2-e]indole;

(7) ethyl(10-benzyl-3,8,9,10,11,12-hexahydro-7H-azepino[4,5-b]pyrano[3,2-e]indol-7-yl)acetate;

(8) (10-benzyl-3,8,9,10,11,12-hexahydro-7H-azepino[4,5-b]pyrano[3,2-e]indol-7-yl)acetic acid;

(9) 2-(10-benzyl-3,8,9,10,11,12-hexahydro-7H-azepino[4,5-b]pyrano[3,2-e]indol-7-yl)-N-phenylacetamide; or

(10) 2-(1,2,3,8,9,10,11,12-octahydro-7H-azepino[4,5-b]pyrano[3,2-e]indol-7-yl)-N-phenylacetamide;

or a pharmaceutically acceptable salt or solvate thereof.

Another preferred compound of the invention is:

(1) 3,3-dimethyl-2,3,7,8,9,10,11,12-octahydro-1H-azepino[4,5-b]pyrano[3,2-e]indole;

(2) 10-benzyl-3,3-dimethyl-7,8,9,10,11,12-hexahydro-3H-azepino[4,5-b]pyrano[3,2-e]indole;

(3) 7-phenyl-2,3,7,8,9,10,11,12-octahydro-1H-azepino[4,5-b]pyrano[3,2-e]indole;

(4) 7-benzyl-2,3,7,8,9,10,11,12-octahydro-1H-azepino[4,5-b]pyrano[3,2-e]indole; or (5) rac-cis-2,3,7,7a,8,9,10,11,12,12a-decahydro-1H-azepino[4,5-b]pyrano[3,2-e]indole;

or a pharmaceutically acceptable salt or solvate thereof.

A more preferred compound of the invention is 2,3,7,8,9,10,11,12-octahydro-1H-azepino[4,5-b]pyrano[3,2-e]indole; or a pharmaceutically acceptable salt or solvate thereof.

Compounds of Formula (I) can be prepared by any suitable method known in the art, or by the following reaction sequence which forms part of the present invention. All of the starting materials are commercially available, or are prepared by procedures described herein or by procedures that would be well known to one of ordinary skill in organic and/or pharmaceutical chemistry. In the methods below, $R^1$, $R^2$, $R^3$, $R^4$, $R^a$, and $R^b$ are as defined in structural Formula (I) above.

It should be understood that protecting groups can be utilized in accordance with general principles of organic synthetic chemistry to provide compounds of structural Formula (I). Protecting compounds and protecting groups are well known to persons skilled in the art. See e.g., T. W. Greene et al., "Protective Groups in Organic Synthesis; Second Edition," John Wiley and Sons, Inc., New York, N.Y. (1991). These protecting groups are removed when necessary by appropriate basic, acidic, or hydrogenolytic conditions known to persons skilled in the art. Accordingly, compounds of structural Formula (I) not specifically exemplified herein can be prepared by persons skilled in the art.

Compounds of the general structural Formula (I) can be prepared by a number of methods as described hereinafter. For example, one method of synthesizing the compounds of Formula (I) includes demethylation of an azepinoindole of the Structure (1), below, with boron tribromide. (Bz=benzoyl or C(=O)phenyl).

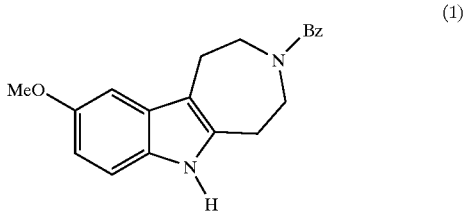

(1)

The azepinoindole structure can be obtained by following the procedures set forth in *J. Org. Chem.*, 1968, 33, 3187–95. Demethylation of the azepinoindole provides Structure (2).

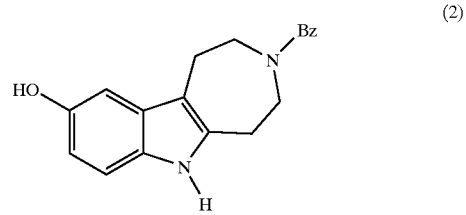

(2)

The demethylated Structure (2) can be alkylated with propargyl bromide in the presence of a base (e.g. potassium or cesium carbonate) in a suitable solvent (e.g. acetone or DMF) to form Structure (3).

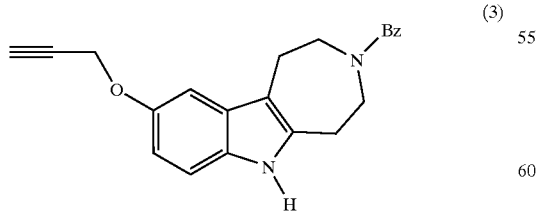

(3)

Structure (3) is subjected to Claisen rearrangement conditions known to persons skilled in the art to provide pyrano structure (4).

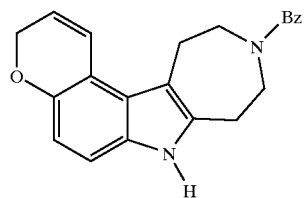

(4)

The pyrano structure (4) is then treated with lithium aluminum hydride to provide the benzyl compound (5), which is a compound of formula (I).

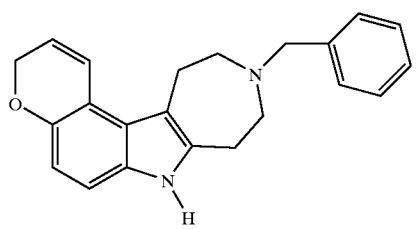

(5)

Compound 5 is hydrogenated in the presence of a suitable catalyst (e.g. palladium-on-carbon) to provide another compound of formula (I).

Alternatively, compounds of Formula (I) can be prepared by the foregoing reactions wherein the azepinoindole of Structure (1), above, is first reacted with sodium hydride and methyl iodide to provide a methylated compound of Structure (1), shown below.

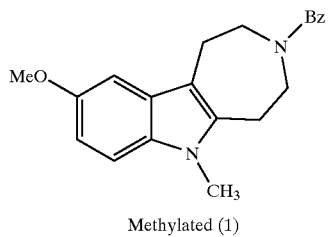

Methylated (1)

Compounds of formula (I) can also be prepared by the foregoing reactions wherein the azepinoindole of structure (5) above is treated with a base (e.g. sodium hydride, sodium carbonate, or cesium carbonate) and an alkylating agent (e.g. $BrCH_2COOEt$, or $BrCH_2CH_2CH_2OPh$) to provide an alkylated structure (6), wherein $R_3$ is other than hydrogen, which is a compound of formula (I).

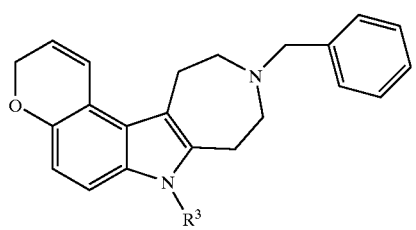

(6)

When $R^3$ is aryl, the reaction can be performed by palladium catalyzed reaction of a compound of structure (5) with an aryl halide or triflate. See for example, D. W. Old, *Org. Lett.*, 2000, 2, 1403. A compound of structure (6) can be converted to other compounds of formula (I) using techniques described herein, or using techniques that are known in the art.

A compounds of formula (I), wherein bond b represented by - - - is a single bond, can be prepared by reduction of bond b in corresponding compound of formula (I) wherein bond b is a double bond. For example, the reduction can be carried out with sodium cyanoborohydride in acetic media such as trifluoroacetic acid or acetic acid.

Compounds of formula (1) can also be prepared by reacting a compound of structure (2) above with an α,β-unsaturated aldehyde or a corresponding acetal (see for example A. Levai, *Heterocycles*, 2000, 53, 1193) in the presence of a suitable acid (e.g. phenylboronic acid and acetic acid, or titanium tetraethoxide, see for example B. A. Chauder, et al., *Synthesis*, 1998, 279; and J. L. Pozzo et al., *J. Chem. Soc., Perkin Trans.* 1, 1994, 2591) to provide a compound of structure (7) in one step.

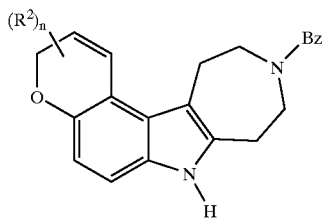

(7)

A compound of structure (7) can be converted to a compound of formula (I) using techniques described herein, or using techniques that are known in the art.

A compound of formula (I) wherein $R^1$ is other than hydrogen can be prepared by alkylating a corresponding compound of structure (8) wherein $R^3$ is not hydrogen with an alkyl halide or an alkyl mesylate in the presence of a base (e.g. triethyl amine or sodium carbonate) and a suitable solvent (e.g. acetonitrile or DMF), or under standard reductive alkylation conditions by treatment with an aldehyde in the presence of sodium cyanoborohydride under acidic conditions (e.g. in the presence of trifluoroacetic acid; see for example Glennon et al., *Med. Chem. Res.*, 1996, 197; and C. F. Lane, *Synthesis*, 1975, 135). When $R^3$ is hydrogen, reductive alkylation is used to introduce $R^1$. For example, a compound of structure (8) can be alkylated to provide a compound of formula (I).

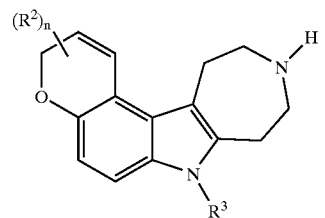

(8)

The phrases "pharmaceutically acceptable salts" or "a pharmaceutically acceptable salt thereof" refer to salts prepared from pharmaceutically acceptable acids or bases, including organic and inorganic acids and bases. Salts can be prepared from pharmaceutically acceptable acids. Pharmaceutically acceptable salts can be obtained using standard procedures known by those skilled in the art, for example by reacting a sufficiently basic compound such as an amine with a suitable acid affording a physiologically acceptable anion. Suitable pharmaceutically acceptable acids include acetic, benzenesulfonic (besylate), benzoic, p-bromophenylsulfonic, camphorsulfonic, carbonic, citric, ethanesulfonic, fumaric, gluconic, glutamic, hydrobromic, hydrochloric, hydroiodic, isethionic, lactic, maleic, malic, mandelic, methanesulfonic (mesylate), mucic, nitric, oxalic, pamoic, pantothenic, phosphoric, succinic, sulfuric, tartaric, p-toluenesulfonic, and the like. Examples of such pharmaceutically acceptable salts, thus, include, but are not limited to, acetate, benzoate, β-hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1, 6-dioate, hydroxybenzoate, iodide, lactate, maleate, malonate, mandelate, metaphosphate, methanesulfonate, methoxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylene sulfonate, and the like. The compounds of the Formula (I) also can provide pharmaceutically acceptable metal salts, in particular alkali metal (e.g., sodium, potassium, magnesium, or lithium) salts and alkaline earth metal (e.g., calcium) salts, with bases.

Compounds of Formula (I) are useful in treating diseases, disorders, and conditions of the central nervous system occurring in mammals. Typically, the mammal is a human being, but the compounds can be used to treat other animals such as livestock, pets, or other animals.

It is to be understood that "a compound of Formula (I)," or a pharmaceutically acceptable (acidic or basic) salt or solvate (i.e., hydrate) thereof, can be administered as the neat compound, or as a pharmaceutical composition containing the compound in combination with a suitable excipient. Such pharmaceutical compositions can be prepared by methods and contain excipients which are known by those skilled in the art. A generally recognized compendium of such methods and ingredients is *Remington's Pharmaceutical Sciences* by E. W. Martin (Mark Publ. Co., 15th Ed., 1975).

The compounds of this invention can be administered in oral unit dosage forms, such as aerosol sprays, buccal tablets, capsules, elixirs, pills, sachets, suspensions, syrups, tablets, troches, wafers, and the like. The compounds also can be administered parenterally, (e.g., subcutaneously, intravenously, intramuscularly, or by intraperitoneal injection), using forms known in the pharmaceutical art. The compounds further can be administered rectally or vaginally, in such forms as suppositories or bougies, transdermally, such as with a "patch" containing active ingredient, or nasally (i.e., by inhalation).

In general, the preferred route of administration of a present compound is oral. For oral administration, the active compound can be combined with one or more excipients and used in the form of ingestible aerosol sprays, buccal tablets, capsules, elixirs, pills, sachets, suspensions, syrups, tablets, troches, wafers, and the like. Such compositions and preparations typically contain at least 0.1% of active compound. The percentage of the compounds in these preparations can be varied, e.g., about 0.01 to about 60% of the weight of a given unit dosage form. The amount of active compound in such orally administered compositions is sufficient to provide an effective dosage level.

The aerosol sprays, buccal tablets, capsules, elixirs, pills, sachets, suspensions, syrups, tablets, troches, wafers, and the like also can contain one or more binders, diluents disintegrating agents, excipients, lubricants, sweetening agents, or flavoring agents. Suitable binders include, for example, gum arabic, tragacanth, acacia, polyvinylpyrrolidone, corn starch, methylcellulose, or gelatin. Suitable diluents include, for example, lactose, dextrose, sucrose, mannitol, sorbitol, and cellulose. Suitable disintegrating agents include, for example, starches, alginic acid, and alginates. Suitable excipients include dicalcium phosphate. Suitable lubricants include, for example, silica, talc, stearic acid, magnesium or calcium stearate, and/or polyethylene glycols. Suitable wetting agents include, for example, lecithin, polysorbates, and laurylsulfates. Generally, any effervescing agents, dyestuffs, and/or sweeteners known by those of ordinary skill in the art can be used in the preparation of a pharmaceutical composition. For example, suitable sweetening agents include sucrose, fructose, lactose or aspartame, and suitable flavoring agents include peppermint, oil of wintergreen, or cherry flavoring. The aforementioned ingredients are merely representative and one skilled in the art could envision other binders, excipients, sweetening agents, and the like.

When the unit dosage form is a capsule, it can contain, in addition to ingredients of the above type, a liquid carrier (e.g., vegetable oil or a polyethylene glycol). Various other ingredients can be present as coatings or to otherwise modify the physical form of the solid unit dosage form. For instance, tablets, pills, or capsules may be coated with gelatin, wax, shellac or sugar, and the like. A syrup or elixir can contain the active compound, sucrose or fructose as a sweetening agent, methyl and propyl parabens as preservatives, a dye and flavoring, such as cherry or orange flavor. Any material used in preparing any unit dosage form should be pharmaceutically acceptable and substantially non-toxic in the amounts employed. In addition, the active compound can be incorporated into sustained-release preparations and devices including, but not limited to, those relying on osmotic pressures to obtain a desired release profile (e.g., the OROS drug delivery devices as designed and developed by Alza Corporation, Mountain View, Calif.).

Orally administered compositions can be prepared by any method that includes the step of bringing the active compound into intimate association with a carrier, which constitutes one or more necessary or desirable ingredients. Generally, the compositions are prepared by uniformly and intimately admixing the active ingredient with liquid carriers, finely divided solid carriers, or both, and then, if necessary, shaping the product into a desired form.

For example, a tablet can be prepared by compression or molding techniques, optionally, using one or more accessory ingredients. Compressed tablets can be prepared by compressing the active ingredient in a suitable machine into a free-flowing form, such as a powder or granules. Thereafter, the compressed, free-flowing form optionally can be mixed with binders, diluents, lubricants, disintegrating agents, effervescing agents, dyestuffs, sweeteners, wetting agents, and non-toxic and pharmacologically inactive substances typically present in pharmaceutical compositions. The pharmaceutical composition can contain about 5 to about 95% compound of the present invention, and preferably from about 25 to about 90% compound of the present invention. Molded tablets can be made by molding a mixture of the powdered compound moistened with an inert liquid diluent in a suitable machine.

Oral administration is the most convenient route of administration and avoids the disadvantages associated with other routes of administration. For patients suffering from a swallowing disorder or from impairment of drug absorption after oral administration, the drug can be administered by other methods, such as parenterally, rectally or vaginally, transdermally, and nasally.

Parenteral administration is performed by preparing the composition containing the active compound. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for parenteral administration (e.g., subcutaneously, intravenously, intramuscularly, or by intraperitoneal injection or infusion) can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage.

The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars, buffers or sodium chloride. Prolonged absorption of the injectable compositions can be achieved by use of agents that delay absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders also can be accomplished through irradiation and aseptic crystallization methods known to persons skilled in the art.

For parenteral administration, the active compounds are presented in aqueous solution in a concentration of about 0.1 to about 10%, more preferably about 0.1 to about 7%, by weight. The solution can contain other ingredients, such as emulsifiers, antioxidants, or buffers.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends, in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Generally, compounds of the invention are serotonin receptor (5-HT) ligands. The ability of a compound of the invention to act as a 5-HT receptor agonist, partial agonist, or antagonist can be determined using in vitro and in vivo assays that are known in the art. For example, see L. W. Fitzgerald et al., *Mol. Pharmacol*, 2000, 57, 1, 75–81; and D. B. Wainscott *J. Pharmacol Exp Ther*, 1996, 276, 2, 720–727. The invention provides compounds of Formula (I) that act as either agonists, partial agonists, or as antagonists of one or more 5-HT receptor subtypes.

The compounds of the invention are useful as modulators of 5-HT receptor function. Thus, the compounds are useful for treating diseases, disorders, and conditions where modulation of 5-HT receptor function is desired. Such diseases, disorders, and conditions include, but are not limited to the following: obesity, depression, schizophrenia, schizophreniform disorder, schizoaffective disorder, delusional disorder, a stress related disease (e.g., general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g., a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disorder or Tardive Dyskinesia), oppositional defiant disorder, peripheral neuropathy, post-traumatic stress disorder, premenstrual dysphoric disorder, a psychotic disorder (brief and long duration disorders and psychotic disorder due to medical condition), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome). Treatment of the above diseases, disorders, and conditions is accomplished by delivering a therapeutically effective amount of the compound of Formula (I) to the mammal.

As used herein, the terms "treat," "treatment," and "treating," extend to prophylaxis, in other words "prevent," "prevention," and "preventing," lowering, stopping, or reversing the progression or severity of the condition or symptoms being treated. As such, the term "treatment" includes both medical therapeutic and/or prophylactic administration, as appropriate. The terms "prevent," "prevention," and "preventing" refer to an administration of the pharmaceutical composition to a person who has in the past suffered from the aforementioned diseases, disorders, or conditions, such as, for example, migraine headaches, but is not suffering from the diseases, disorders, or conditions at the time of the composition's administration.

Compounds and pharmaceutical compositions suitable for use in the present invention include those wherein the active ingredient is administered in an effective amount to achieve its intended purpose. More specifically, a "therapeutically effective amount" means an amount effective to treat the disease, disorder, and/or condition. Determination of a therapeutically effective amounts is well within the capability of persons skilled in the art, especially in light of the detailed disclosure provided herein.

A "therapeutically effective dose" refers to that amount of the compound that results in achieving the desired treatment (or effect). Therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary within this range depending upon the dosage form employed, and the route of administration utilized.

The dosage regimen and amount for treating patients with the compounds of this invention is selected in accordance with a variety of factors including, for example, the type, age, weight, sex, and medical condition of the patient, the severity of the condition, and the route of administration. An ordinarily skilled physician or psychiatrist can readily determine and prescribe an effective amount of the compound to prevent or arrest the progress of the condition. In so proceeding, the physician or psychiatrist can employ relatively low initial dosages and subsequently increasing the dose until a maximum response is obtained.

The compound is administered in unit dosage form, for example, containing about 0.05 mg to about 500 mg, preferably about 0.1 mg to about 250 mg, and more preferably about 1 mg to about 150 mg, of active ingredient per unit dosage form. The desired dose can be presented in a single dose, or as divided doses administered at appropriate intervals, for example, as two, three, four or more sub-doses per day. The sub-dose itself can be further divided, e.g., into a number of discrete loosely spaced administrations.

The compositions can be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

The exact regimen for administration of the compounds and compositions disclosed herein necessarily depends upon the needs of the individual subject being treated, the patient type (i.e., human or animal), the type of treatment and, of course, the judgment of the attending practitioner or physician. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

Specifically, for administration to a human in the curative or prophylactic treatment of the diseases, disorders, and conditions identified above, oral dosages of a compound of Formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required.

For veterinary use, a compound of Formula (I), or a nontoxic salt thereof, is administered as a suitably acceptable formulation in accordance with normal veterinary practice. The veterinarian can readily determine the dosing regimen and route of administration that is most appropriate for a particular animal.

In a particular embodiment, the invention includes a pharmaceutical composition for the curative or prophylactic treatment of diseases, disorders, and conditions, where modulation of 5-HT receptor function is desired, the composition comprising a therapeutically effective amount of a compound of Formula (I), or a pharmaceutically acceptable salt or solvate thereof, together with a pharmaceutically acceptable diluent or carrier.

The following examples are provided to illustrate the invention but are not intended to limit the scope of the invention.

EXAMPLES

The following abbreviations are used hereafter in the accompanying examples: $\mu$M (micromole), Bn (benzyl), Bz (benzoyl), cm (centimeter), DMSO (dimethyl sulfoxide), Et$_3$N (triethylamine), EtOAc (ethyl acetate), g. (gram), IR (infrared), KBr (potassium bromide), m.p. (melting point), MeOH (methanol), MgSO$_4$ (magnesium sulfate), MHz (megahertz), min. (minute), mL (milliliter), mmol (millimole), NMR (nuclear magnetic resonance), and psi (pounds per square inch).

Example 1

10-Benzyl-7-methyl-7,8,9,10,11,12-hexahydro-3H-azepino[4,5-b]pyrano[3,2-e]indole.

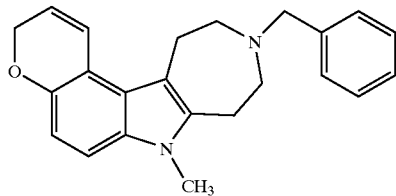

To a solution of the azepino[4,5-b]pyrano[3,2-e]indole compound from sub-part d (1.79 g., 4.98 mmol) in tetrahydrofuran (50.0 mL) was added lithium aluminum hydride (1.89 g., 49.8 mmol). The resulting mixture was stirred at room temperature for 16 hours. Water (1.89 mL), 15% sodium hydroxide solution (1.89 mL), and water (5.00 mL) then were added to the mixture sequentially. The resulting mixture was filtered through a pad of celite, and the filtrate was concentrated in vacuo. The residue was subjected to column chromatography (silica gel, 50% EtOAc/hexane, 1% Et$_3$N) to yield the benzyl compound (0.87 g, 51%) as a colorless solid. M.p. 112–114° C. (EtOAc/hexane); IR (KBr) 3081, 3058, 3029, 3022, 1634, 1593, 1576, 1550, 1494, 1467, 1454, 1368, 1230,1108 cm$^{-1}$; $^1$H NMR (400 MHz, CDCl$_3$) $\delta$ 7.42–7.40, 7.36–7.33, 7.29–7.25, 7.12, 6.99, 6.71, 5.81, 4.67–4.65, 3.80, 3.57, 3.17–3.14, 3.00–2.95, 2.84–2.81, 2.78–2.75, 2.65–2.62; $^{13}$C NMR (DMSO-d$_6$) $\delta$ 148.5, 139.7, 137.2, 132.4, 129.0, 128.3, 127.0, 123.5, 123.1, 119.3, 114.1, 112.8, 110.1, 109.2, 64.6, 61.4, 55.2, 53.1, 29.5, 25.3, 25.0; HRMS (FAB) cacld for C$_{23}$H$_{24}$N$_2$O+H: 345.1967, found: 345.1976.

The intermediate azepino[4,5-b]pyrano[3,2-e]indole was prepared as follows.

a. 3-Benzoyl-9-methoxy-6-methyl-1,2,3,4,5,6-hexahydroazepino[4,5-b]indole.

To a solution of 3-benzoyl-9-methoxy-1,2,3,4,5,6-hexahydroazepino[4,5-b]indole (U.S. Pat. No. 3,839,357) (10.90 g., 34.01 mmol) in N,N-dimethylformamide (340.0 mL) was added sodium hydride (1.50 g., 60% in oil, 37.41 mmol) at 0° C. The mixture was stirred at room temperature for 20 minutes and cooled to 0° C. After the addition of methyl iodide (2.54 mL, 5.79 g., 40.81 mmol), the resulting mixture was stirred at room temperature for 16 hours. Water (400.0 mL) and ethyl acetate (400.0 mL) then were added, and the organic and aqueous phases separated. The aqueous layer was extracted with ethyl acetate (2×). The combined ethyl acetate solution was dried (MgSO$_4$) and filtered. The filtrate was concentrated in vacuo. The residue was subjected to column chromatography (silica gel, 50% EtOAc/hexane) to yield the methylated compound (9.96 g, 87%) as a yellowish oil. IR (liq.) 2937, 2906, 1629, 1601, 1579, 1486, 1462, 1445, 1424, 1381, 1375, 1347, 1299, 1288, 1271, 1246, 1229,1156, 1143, 1047,1035, 1031, 789, 727, 707 cm$^{-1}$; $^1$H NMR (300 MHz, CDCl$_3$) $\delta$ 7.43–7.39, 7.17–7.12, 6.97–6.82, 4.09–4.00, 3.93–3.88, 3.76–3.57, 3.21–3.11, 2.92–2.87; MS (ESI+) m/z 335 (M$^+$+H); HRMS (FAB) cacld for C$_{21}$H$_{22}$N$_2$O$_2$+H: 335.1759, found: 335.1754.

b. 3-Benzoyl-9-hydroxy-6-methyl-1,2,3,4,5,6-hexahydroazepino[4,5b]indole.

To a solution of the methylated compound from sub-part a (13.0 g., 38.9 mmol) in dichloromethane (400 mL) was added boron tribromide (7.35 mL, 19.5 g., 77.8 mmol) at 0° C. The resulting mixture was stirred at room temperature for 36 hours. Ammonium chloride solution (10.0 mL) and water (400 mL) then were added sequentially. After separation of the organic and liquid phases, the aqueous layer was extracted with dichloromethane (2×). The combined dichloromethane solution was dried (MgSO$_4$) and filtered. The filtrate was concentrated in vacuo and the residue was subjected to column chromatography (silica gel, 70% EtOAc/hexane) to yield the alcohol as a yellowish solid. M.p. 138–141° C.; IR (KBr) 3491, 3358, 3270, 3070, 3067, 2982, 2951, 2936, 2886, 2837, 1626, 1588, 1501, 1467, 1372, 1349, 1343, 1289, 1278, 1245, 1212, 1158, 1145, 840, 748, 708, 701 cm$^{-1}$; $^1$H NMR (400 MHz, DMSO-d$_6$) $\delta$ 7.43–7.39, 7.05, 6.85–6.67, 4.06–3.90, 3.71–3.55, 3.16–3.03, 2.86–2.81; MS m/z 320 (M$^+$); HRMS (FAB) cacld for C$_{20}$H$_{20}$N$_2$O$_2$+H: 321.1603, found: 321.1614; Anal. Calcd. for C$_{20}$H$_{20}$N$_2$O$_2$: C, 74.98; H, 6.29; N, 8.74. Found: C, 74.79; H, 6.33; N, 8.66.

c. 3-Benzoyl-6-methyl-9-(2-propynyloxy)-1,2,3,4,5,6-hexahydroazepino[4,5-b]indole.

A mixture of the alcohol from sub-part b (3.78 g., 11.8 mmol), propargyl bromide (1.58 mL, 2.10 g., 80%, 14.1 mmol), and cesium carbonate (11.5 g., 35.4 mmol) in acetone (118 mL) was stirred at room temperature for 48 hours. After filtration through a pad of celite, the filtrate was concentrated in vacuo and the residue was subjected to column chromatography (silica gel, 50% EtOAc/hexane) to yield the propargyl ether (3.06 g, 72%) as a light yellow foam. IR (KBr) 3282, 3228, 3100, 3079, 3058, 3026, 2974, 2932, 2839, 2575, 2478, 2337, 2116, 1625, 1601, 1577, 1511, 1484, 1464, 1445, 1424, 1383, 1375, 1348, 1299, 1290, 1271, 1246, 1220, 1213, 1155, 1145, 1046, 1027, 928, 790, 708, 630 cm$^{-1}$; $^1$H NMR (300 MHz, CDCl$_3$) δ 7.48–7.41, 7.18–7.14, 7.07–6.88, 4.74–4.68, 4.11–4.00, 3.72–3.57, 3.21–3.12, 2.91–2.87, 2.52–2.48.

d. 10-Benzoyl-7-methyl-7,8,9,10,11,12-hexahydro-3H-azepino[4,5-b]pyrano[3,2-e]indole.

A solution of the propargyl ether from sub-part c (0.23 g., 0.65 mmol) in bromobenzene (7.0 mL) was refluxed for 24 hours. After cooling to room temperature, bromobenzene was removed in vacuo. The residue was subjected to column chromatography (silica gel, 60% EtOAc/hexane) to yield the azepino[4,5-b]pyrano[3,2-e]indole compound as a yellowish solid. M.p.>177° C.; $^1$H NMR (300 MHz, CDCl$_3$) δ 7.42, 7.05–6.97, 6.74, 5.93–5.74, 4.69–4.65, 4.12–4.05, 3.80–2.92. MS (ESI+) m/z 381 (M$^+$+Na). Anal. Calcd. for C$_{23}$H$_{22}$N$_2$O$_2$.H$_2$O: C, 73.38; H, 6.43; N, 7.44. Found: C, 72.92; H, 6.03; N, 7.35.

Example 2

7-Methyl-2,3,7,8,9,10,11,12-octahydro-1H-azepino[4.5-b]pyrano[3,2-e]indole Hydrochloride

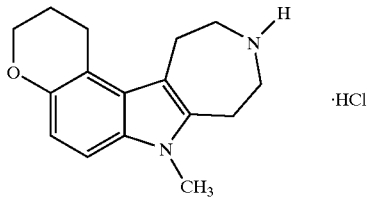

A solution containing 10-benzyl-7-methyl-7,8,9,10,11,12-hexahydro-3H-azepino[4,5-b]pyrano[3,2-e]indole (0.18 g., 0.51 mmol, Example 1) in ethanol (20.0 mL) was hydrogenated in the presence of palladium-on-carbon (0.07 g.) and 2 N hydrochloric acid (0.51 mL, 0.51 mmol) at 50 psi for 48 hours. After filtration through a pad of celite, the filtrate was concentrated in vacuo. The residue was recrystalized from EtOAc/MeOH to yield the title compound (0.13 g, 84%) as a light yellow solid. M.p.>217° C. (dec.); IR (KBr) 2946, 2877, 2844, 2809, 1609, 1585, 1551, 1467, 1447, 1280, 1267, 1255, 1238, 1109, 787 cm$^{-1}$; $^1$H NMR (300 MHz, DMSO-d$_6$) δ 7.07, 6.52, 4.04–4.01, 3.57, 3.31–3.28, 3.19–3.12, 3.07–3.03, 1.96–1.92; $^{13}$C NMR (DMSO-d$_6$) δ 148.5, 136.8, 131.2, 125.2, 112.3, 112.1, 110.9, 108.8, 65.4, 46.3, 44.2, 29.7, 23.1, 22.6, 22.4; MS (ESI+) m/z 257 (M$^+$+H); HRMS cacld for C$_{16}$H$_{20}$N$_2$O+H: 257.1654, found: 257.1646; Anal. Calcd. for C$_{16}$H$_{20}$N$_2$O.HCl.H$_2$O: C, 61.83; H, 7.46; N, 9.01. Found: C, 62.07; H, 7.41; N, 9.01.

The intermediate compound 10-benzoyl-7-methyl-7,8,9,10,11,12-hexahydro-3H-azepino[4,5-b]pyrano[3,2-e]indole was prepared as described in Example 1.

Example 3

10-Benzyl-7,8,9,10,11,12-hexahydro-3H-azepino[4,5-b]pyrano[3,2-e]indole

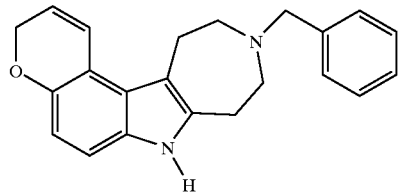

To a solution of 10-benzoyl-7,8,9,10,11,12-hexahydro-3H-azepino[4,5-b]pyrano[3,2-e]indole from sub-part c (0.82 g., 5.88 mmol) in tetrahydrofuran (25.0 mL) was added lithium aluminum hydride (0.91 g., 23.8 mmol). The resulting mixture was stirred at room temperature for 16 hours. Water (0.91 mL), 15% sodium hydroxide solution (0.91 mL), and water (2.70 mL) then were added to the mixture sequentially. The resulting mixture was filtered through a pad of celite, and the filtrate was concentrated in vacuo. The residue was subjected to column chromatography (silica gel, 50% EtOAc/hexane, 1% Et$_3$N) to yield the benzyl compound (0.64 g, 81%) as a colorless solid. M.p. 157–160° C. (CH$_2$Cl$_2$/hexane); $^1$H NMR (300 MHz, CDCl$_3$) δ 7.78, 7.45, 7.39–7.30, 7.68–7.01, 6.67, 5.81, 4.67, 3.88, 3.22–3.11, 3.11–2.93; HRMS (FAB) calcd for C$_{22}$H$_{22}$N$_2$O+H: 331.1810, found 331.1817; Anal. Calcd. for C$_{22}$H$_{22}$N$_2$O: C, 79.97; H, 6.71; N, 8.48. Found: C, 79.49; H, 6.77; N, 8.37.

The intermediate 10-benzoyl-7,8,9,10,11,12-hexahydro-3H-azepino[4,5-b]pyrano[3,2-e]indole was prepared as follows.

a. 3-Benzoyl-9-hydroxy-1,2,3,4,5,6-hexahydroazepino[4,5-b]indole.

To a solution of 3-benzoyl-9-methoxy-1,2,3,4,5,6-hexahydroazepino[4,5-b]indole (8.43 g., 26.3 mmol) in dichloromethane (260 mL) was added boron tribromide (2.61 mL, 6.93 g., 27.6 mmol) at 0° C. The resulting mixture was stirred at room temperature for 16 hours. Water (300 mL) then was added. The resulting solid was filtered and collected to yield the hydroxy compound as a light grey solid. M.p. 194–195° C.; IR (KBr) 3381, 3325, 3261, 3252, 3085, 3061, 3025, 2997, 2975, 2934, 2903, 2873, 2843, 1627, 1595, 1496, 1493, 1468, 1372, 1294, 1286, 1277, 1244, 1222, 1196, 1157, 850, 838, 809, 786, 744, 705 cm$^{-1}$; $^1$H NMR (300 MHz, DMSO-d$_6$) δ 10.51–10.42, 8.31, 7.47–7.39, 7.04, 6.73–6.62, 6.53–6.50, 3.85, 3.51, 3.02, 2.87, 2.78, 2.64; MS (ESI+) m/z 307 (M$^+$+H). HRMS cacld for C$_{19}$H$_{18}$N$_2$O$_2$+H: 307.1446, found: 307.1455; Anal. Calcd. for C$_{19}$H$_{18}$N$_2$O$_2$+H$_2$O: C, 70.35; H, 6.21; N, 8.64. Found: C, 70.13; H, 5.70; N, 8.45.

b. 3-Benzoyl-9-(2-propynyloxy)-1,2,3,4,5,6-hexahydro-azepino[4,5-b]indole.

A mixture of the hydroxy compound from sub-part a (8.00 g., 26.0 mmol), propargyl bromide (3.48 mL, 3.71 g., 80%, 31.2 mmol), and cesium carbonate (33.9 g., 104 mmol) in acetone (260 mL) was stirred at room temperature for 48 hours. After filtration through a pad of celite, the filtrate was concentrated in vacuo to dryness and the residue was subjected to column chromatography (silica gel, 60% EtOAc/hexane) to yield the propargyl ether (6.34 g, 71%) as a colorless solid. M.p. 167–168° C.; IR (KBr) 3262, 3222, 3062, 3045, 2950, 2909, 2886, 2841, 2113, 1609, 1583, 1577, 1495, 1467, 1456, 1443, 1286, 1268, 1248, 830, 811, 788, 740, 706, 699, 684, 674, 632 cm$^{-1}$; $^1$H NMR (300

MHz, CDCl₃) δ 7.89–7.70, 7.42, 7.19–7.16, 7.06–6.84, 4.74–4.69, 4.14–3.98, 3.70–3.62, 3.20–3.05, 2.88–2.76, 2.52–2.48. MS (ESI+) m/z 345 (M⁺+H); HRMS cacld for C₂₁H₁₈N₂O₂+H: 345.1603, found: 345.1605; Anal. Calcd. for C₂₁H₁₈N₂O₂: C, 76.34; H, 5.49; N, 8.48. Found: C, 76.17; H, 5.83; N, 7.93.

c. 10-benzoyl-7,8,9,10,11,12-hexahydro-3H-azepino[4,5-b]pyrano[3,2-e]indole.

A solution of the propargyl ether from sub-part b (5.51 g., 16.0 mmol) in bromobenzene (160 mL) was refluxed for 24 hours. After cooling to room temperature, the bromobenzene was removed in vacuo. The residue was subjected to column chromatography (silica gel, 70%EtOAC/Hex) to yield the azepino[4,5-b]pyrano[3,2-e]indole compound (5.50 g, 99%) as a yellowish solid. M.p. 241–243° C.; IR (KBr) 3265, 3064, 3050, 2975, 2951, 2928, 2898, 2840, 1615, 1602, 1579, 1493, 1465, 1273, 1246, 1220, 1100, 788, 738, 704, 697 cm⁻¹; ¹H NMR (300 MHz, CDCl₃) δ 7.88–7.62, 7.42, 7.17–6.91, 6.70, 5.91–5.74, 4.72–4.63, 4.08–3.96, 3.82–3.73, 3.42–2.80. MS(ESI+) m/z 345 (M⁺+H); HRMS (FAB) cacld for C₂₂H₂₀N₂O₂+H: 345.1603, found: 345.1611; Anal. Calcd. for C₂₂H₂₀N₂O₂: C, 76.72; H, 5.85; N, 8.13. Found: C, 76.31; H, 6.02; N, 7.98.

Example 4

2,3,7,8,9,10,11,12-Octahydro-1H-azepino[4,5-b]pyrano[3,2-e]indole Hydrochloride

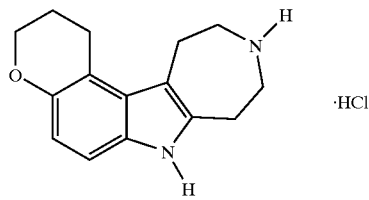

A solution of 10-benzyl-7,8,9, 10,11,12-hexahydro-3H-azepino[4,5-b]pyrano[3,2-e]indole (0.38 g., 1.17 mmol, Example 3) in ethanol (20.0 mL) was hydrogenated in the presence of palladium-on-carbon (0.20 g.) and 2N hydrochloric acid (0.58 mL, 1.17 mmol) at 55 psi for 24 hours. After filtration through a pad of celite, the filtrate was concentrated in vacuo. The residue was recrystalized from EtOAc/MeOH to yield the title compound (0.31 g, 94%) as a light yellow solid. M.p.>283° C. (dec.); IR (KBr) 3235, 3229, 2983, 2957, 2946, 2926, 2877, 2855, 2817, 2752, 2738, 2717, 2681, 2639, 2600, 2540, 1585, 1497, 1454, 1435, 1430, 1225, 1186, 1089, 805 cm⁻¹; ¹H NMR (400 MHz, DMSO-d₆) δ 10.82, 9.55, 6.95, 6.48, 4.04–4.02, 3.30–3.23, 3.13–3.10, 3.07–3.04, 1.99–1.93; ¹³C NMR (DMSO-d₆) δ 147.7, 135.1, 129.4, 125.9, 111.6, 111.5, 110.2, 109.6, 64.8, 46.3, 44.4, 24.3, 22.7, 22.5, 22.2; MS (ESI+) m/z 243 (M⁺+H); HRMS (FAB) cacld for C₁₅H₁₈N₂O+H: 243.1497, found: 243.1500; Anal. Calcd. for C₁₅H₁₈N₂O.HCl: C, 64.63; H, 6.87; N, 10.05. Found: C, 64.23; H, 6.95; N, 9.87.

The intermediate 10-benzyl-7,8,9,10,11,12-hexahydro-3H-azepino[4,5-b]pyrano[3,2-e]indole was prepared as described in Example 3.

Example 5

10-Benzyl-7-(4-phenoxybutyl)-7,8,9,10,11,12-hexahydro-3H-azepino[4,5-b]pyrano[3,2-e]indole.

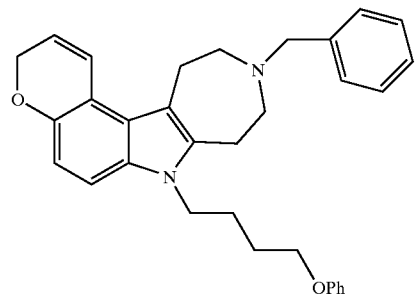

To a solution containing the compound of Example 3 (0.08 g., 0.24 mmol) in N,N-dimethylformamide (5.00 mL) was added sodium hydride (0.011 g., 60% in oil, 0.29 mmol) at 0° C. The mixture was stirred at room temperature for 20 minutes, then cooled to 0° C. 4-Phenoxybutyl bromide (0.072 g., 0.32 mmol) was added to the mixture, the resulting mixture was stirred at room temperature for 16 hours. Water and ethyl acetate then were added to the mixture, and the organic and aqueous phases were separated. The aqueous layer then was extracted with ethyl acetate (2x). The combined ethyl acetate solution was dried (MgSO₄) and filtered. The filtrate was concentrated in vacuo. The residue was subjected to preparative thin layer chromatography (silica gel, 50% EtOAc/hexane) to yield the alkylated compound (0.033 g, 29%) as a light yellow oil. ¹H NMR (300 MHz, CDCl₃) δ 7.42, 7.13, 7.03, 6.95, 6.87, 6.71, 5.81, 4.69–4.67, 4.09, 3.93, 3.75, 3.17–3.14, 2.97–2.94, 1.87–1.76; MS (ESI+) m/z 479 (M⁺+1).

Example 6

7-(4-Phenoxybutyl)-2,3,7,8,9,10,11,12-octahydro-1H-azepino[4,5-b]pyrano[3,2-e]indole Hydrochloride

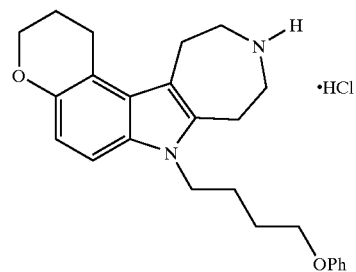

A solution containing 10-benzyl-7-(4-phenoxybutyl)-7,8,9,10,11,12-hexahydro-3H-azepino[4,5-b]pyrano[3,2-e]indole (0.085 g., 0.18 mmol, Example 5) in ethanol (10.0 mL) was hydrogenated in the presence of palladium-on-carbon (0.04 g.) and 2 N hydrochloric acid (0.09 mL, 0.18 mmol) at 50 psi for 16 hours. After filtration through a pad of celite, the filtrate was concentrated in vacuo. The residue was recrystalized from EtOAc/MeOH to yield the title compound (0.075 g, 99%) as a light yellow solid. ¹H NMR (300 MHz, MeOH-d₄) δ 7.24–7.19, 7.03, 6.90–6.80, 6.57, 4.18–4.06, 3.85, 3.47–3.32, 3.28–3.17, 3.11, 2.04–1.95, 1.89–1.65, 1.40–1.25, 0.95–0.81; MS (ESI+) m/z 391 (M⁺+H).

Example 7

Ethyl (10-benzyl-3,8,9,10,11,12-hexahydro-7H-azepino[4,5-b]pyrano[3.2-e]indol-7-yl)acetate

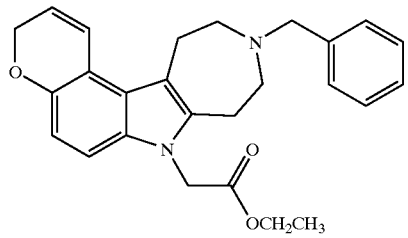

To a suspension of sodium hydride (0.076 g., 60% dispersion in mineral oil) in N,N-dimethylformamide (3.00 mL) was added a solution containing the compound of Example 3 (0.57 g., 1.70 mmol) in N,N-dimethylformamide (5.00 mL) at 0° C. The mixture was stirred at room temperature for 30 minutes, then ethyl bromoacetate (0.23 mL, 2.07 mmol) was added to the mixture, and stirring was continued at room temperature for 18 hours. Water then was added to the mixture, and the resulting mixture was partitioned between ethyl acetate (organic layer) and water. The organic layer was washed several times with water, then concentrated in vacuo. The residue was subjected to column chromatography (silica gel, 10–40% EtOAc/heptane) to yield the acetate compound (0.34 g, (47%) as a light yellow oil. $^1$H NMR (300 MHz, CDCl$_3$) δ 7.42, 7.35, 7.29, 7.10, 6.93, 6.71, 5.83, 4.71, 4.67, 4.18, 3.82, 3.25–3.14, 3.11–2.84, 1.25; MS (ESI+) m/z 417 (M+H), HRMS (FAB) calcd for $C_{26}H_{28}N_2O_3$+H: 417.2178, found 417.2183.

Example 8

10-Benzyl-3,8,9,10,11,12-hexahydro-7H-azepino[4,5-b]pyrano[3,2-e]indol-7-yl)acetic Acid

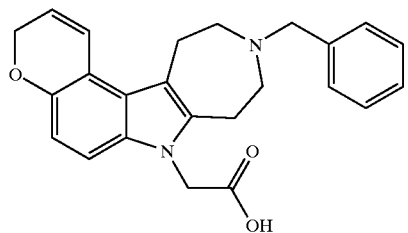

The compound from Example 7 (0.29 g, 0.70 mmol) was dissolved in ethanol (5.00 mL). Lithium hydroxide monohydrate (0.044 g, 1.00 mmol) was added to the solution, and the solution turned red. The solution was stirred at room temperature for 4 hours, concentrated, and partitioned between ethyl acetate and 1 N hydrochloric acid. The organic layer was washed with water and concentrated in vacuo to yield the acid (0.12 g) as a yellow solid. M.p. 185–187° C.; HPLC Ret. Time=2.91 minutes; MS (ESI+) m/z 389 (M+H); HRMS (FAB) calcd for $C_{24}H_{24}N_2O_3$+H: 389.1865, found 389.1877.

Example 9

2-(10-benzyl-3,8,9,10,11,12-hexahydro-7H-azepino[4.5-b]pyrano[3,2-e]indol-7-yl)-N-phenylacetamide

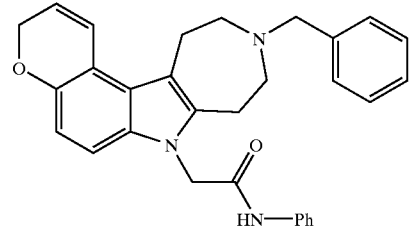

A mixture containing the acid from Example 8 (0.12 g., 0.309 mmol), 1-(3-dimethylaminopropyl)3-ethylcarbodiimide hydrochloride (0.071 g., 0.37 mmol, Example 8), and aniline (0.035 g., 0.37 mmol) in N,N-dimethylformamide (7.00 mL) was stirred at room temperature for 18 hours. The mixture then was poured into a 1:1 solution of water/saturated sodium bicarbonate, to form a precipitate which then was filtered to provide the amide (0.085 g) as a light brown solid. M.p. 134–136° C.; MS (ESI+) m/z 464 (M+H); HRMS (FAB) calcd for $C_{30}H_{29}N_3O_2$+H 464.2338, found 464.2345.

Example 10

2-(1,2,3,8,9,10,11,12-Octahydro-7H-azepino[4.5-b]pyrano[3,2-e]indol-7-yl)-N-phenylacetamide Hydrochloride

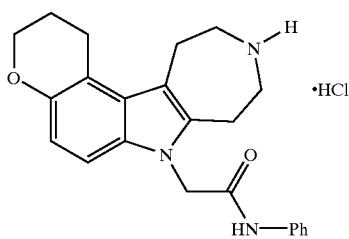

A mixture containing 2-(10-benzyl-3,8,9,10,11,12-hexahydro-7H-azepino[4,5-b]pyrano[3,2-e]indol-7-yl)-N-phenylacetamide (0.078 g., 0.30 mmol, Example 9), 1 N hydrochloric acid (0.17 mL, 0.17 mmol, Example 9), and palladium-on-carbon (10%, 0.25 g.) in ethanol (50 mL) was placed on a Parr hydrogenator under 50 psi of hydrogen and shaken for 52 hours. The reaction mixture then was filtered through celite, and concentrated in vacuo to provide a gray solid (0.025 g, 36%). Crystallization from MeOH/Et$_2$O yielded the title compound (0.005 g) as a dark gray solid. M.p.>250° C. (dec.); HPLC Ret. Time=2.99 min.; HRMS (FAB) calcd for $C_{23}H_{25}N_3O_2$+H: 376.2025, found 376.2032.

Example 11

10-Benzyl-3,3-dimethyl-7,8,9,10,11,12-hexahydro-3H-azepino[4,5-b]pyrano[3,2-e]indole.

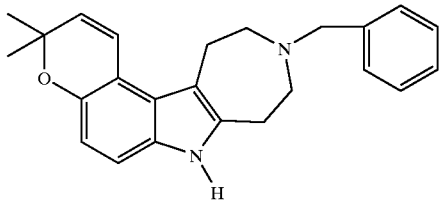

To a solution of 10-benzoyl-3,3-dimethyl-7,8,9,10,11,12-hexahydro-3H-azepino[4,5-b]pyrano[3,2-e]indole (0.115 g, 0.31 mmol) in tetrahydrofuran (5.0 mL) was added lithium aluminum hydride (0.125 g, 3.10 mmol). The resulted mixture was stirred at room temperature for 16 h. Water (0.13 mL), 15% sodium hydroxide solution (0.13 mL) and water (0.39 mL) were added sequentially. The mixture was filtered through a pad of celite and the filtrate was concentrated in vacuo to dryness. The residue was subjected to prep TLC (25% EtOAc/hexane, 1% Et$_3$N) to afford 0.067 g (60%) of light yellow solid as the title compound: $^1$H NMR (300 MHz, CDCl$_3$) δ 7.68, 7.47–7.30, 7.06–7.02, 6.69, 5.63, 3.85, 3.18–3.16, 3.05–2.88, 1.49; $^{13}$C NMR (DMSO-d$_6$) δ 147.3, 139.5, 138.2, 130.8, 129.4, 129.2, 128.7, 127.5, 124.7, 120.9, 113.5, 113.2, 111.9, 110.0, 75.0, 61.4, 55.8, 54.0, 28.6, 27.4, 26.2; MS (ESI+) m/z 373 (M$^+$+H).

The intermediate 10-benzoyl-3,3-dimethyl-7,8,9,10,11,12-hexahydro-3H-azepino[4,5-b]pyrano[3,2-e]indole was prepared as follows.

a. 10-benzoyl-3,3-dimethyl-7,8,9,10,11,12-hexahydro-3H-azepino[4,5-b]pyrano[3,2-e]indole A mixture of 3-benzoyl-9-hydroxy-1,2,3,4,5,6-hexahydroazepino[4,5-b]indole (0.306 g, 1.0 mmol), 3-methyl-2-butenal (0.11 mL, 1.1 mmol), phenylboronic acid (0.134 g, 1.1 mmol) and glacial acetic acid (5.0 mL) in anhydrous toluene (37.0 mL) was refluxed for 3 hours under nitrogen in an apparatus fitted with a Dean-Stark trap. After cooling down to room temperature, the mixture was concentrated in vacuo to dryness, the residue was partitioned between water (30.0 mL) and dichloromethane (30.0 mL). The aqueous layer was extracted with dichloromethane (2×30.0 mL). The combined dichloromethane solution was washed with water and NaHCO$_3$ solution successfully, dried (MgSO$_4$) and filtered. The filtrate was concentrated in vacuo to dryness and the residue was subjected to column chromatography (EtOAc:hexane, 1:1) to give 0.128 g (34%) of 10-benzoyl-3,3-dimethyl-7,8,9,10,11,12-hexahydro-3H-azepino[4,5-b]pyrano[3,2-e]indole as a light yellow solid: $^1$H NMR (300 MHz, CDCl$_3$) δ 7.99–7.82, 7.35, 6.94–6.89, 6.76, 6.58, 5.57–5.46, 4.02–3.92, 3.64–3.56, 3.29, 3.05–2.99, 2.78, 1.38, 1.34; MS (ESI+) m/z 373 (M$^+$+H).

Example 12

3,3-dimethyl-2,3,7,8,9,10,11,12-octahydro-1H-azepino[4,5-b]pyrano[32-e]indole Hydrochloride

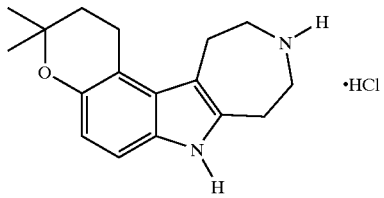

A solution of 10-benzyl-3,3-dimethyl-7,8,9,10,11,12-hexahydro-3H-azepino[4,5-b]pyrano[3,2-e]indole (0.065 g, 0.18 mmol, Example 11) in ethanol (20.0 mL) was hydrogenated in the presence of palladium on carbon (0.035 g) and 2 N hydrochloric acid (0.09 mL, 0.1 8 mmol) at 55 psi for 3 days. Palladium on carbon (0.035 g) was added and continued hydrogenation for another 4 days. After filtration through a pad of celite, the filtrate was concentrated in vacuo to dryness. The residue was recrystallized from EtOAc/MeOH to give 0.017 g (30%) of colorless solid as the desired product: mp>258° C. (dec.); $^1$H NMR (300 MHz, MeOH-d$_4$) δ 7.00, 6.52, 3.47, 3.22–3.13, 1.89–1.85, 1.33; MS (ESI+) m/z 271 (M$^+$+H).

Example 13 rac-cis-2,3,7,7a,8,9,10,11,12,12a-decahydro-1H-azepino[4,5-b]pyrano[3,2-e]indole.

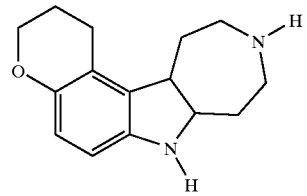

To a solution of 2,3,7,8,9,10,11,12-octahydro-1H-azepino[4,5-b]pyrano[3,2-e]indole hydrochloride (1.39 g, 5.00 mmol, Example 4) in trifluoroacetic acid (50.0 mL) was added freshly prepared solution of sodium cyanoborohydride (1.86 g, 30.00 mmol) in MeOH (5.0 mL) at 0° C. dropwise. The mixture was stirred at room temperature for 30 minutes. Water (30.0 mL) was added followed by the addition of 20% NaOH until basic. The mixture was then extracted with dichloromethane (3×). The combined organic solution was dried (MgSO$_4$) and filtered. The filtrate was concentrated in vacuo to dryness. The residue was subjected to column chromatography (silica gel, 2% MeOH/CHCl$_3$ with 1% of NH$_4$OH) to give 0.48 g (39%) of foam as the title compound. IR (KBr) 3388, 3289, 3243, 3034, 2966, 2942, 2922, 2848, 1476, 1450, 1293, 1273, 1263, 1244, 1201, 1091, 1071, 807 cm$^-$; $^1$H NMR (300 MHz, CDCl$_3$) δ 6.58–6.57, 6.46–6.44, 4.26–4.16, 4.09–4.06, 3.52, 3.51–3.44, 3.20–3.13, 2.85–2.69, 2.27–2.15, 2.05–1.95, 1.83–1.80; $^{13}$C NMR (125.7 MHz, CDCl$_3$) δ 149.0, 143.6, 131.4, 119.6, 116.2, 109.2, 66.2, 61.9, 51.2, 47.5, 45.6, 44.0, 33.2, 30.1, 22.8, 22.7; MS (ESI+) m/z 245 (M$^+$+H); HRMS (FAB) calcd for C$_{15}$H$_{20}$N$_2$O+H: 245.1654, found: 245.1642.

The Examplified compounds are 5-HT ligands, with the ability to displace >50% of a radiolabeled test ligand from one or more 5-HT receptor subtypes at a concentration of 1

μM. The procedures used for testing such displacement are well known and readily available to persons skilled in the art. For example, see L. W. Fitzgerald et al., *Mol. Pharmacol*, 2000, 57, 1, 75–81; and D. B. Wainscott *J. Pharmacol Exp Ther*, 1996, 276, 2, 720–727.

All publications, patents, and patent documents are incorporated by reference herein, as though individually incorporated by reference. The invention has been described with reference to various specific and preferred embodiments and techniques. However, it should be understood that many variations and modifications can be made while remaining within the spirit and scope of the invention.

What is claimed is:

1. A compound of formula (I):

(I)

wherein:
- $R^1$ is selected from the group consisting of H, $C_{1-8}$alkyl and $C_{1-8}$alkylenearyl;
- each $R^2$, independently, is selected from the group consisting of halo, $C_{1-8}$alkyl, $C_{1-8}$alkoxy, aryl, and OH;
- $R^3$ is selected from the group consisting of hydrogen, $C_{1-8}$alkyl, aryl, heteroaryl, $C(=O)R^a$, $C(=O)OR^a$, $C(=O)NR^aR^b$, $C(=O)SR^a$, $C(=S)NR^aR^b$, $SO_2R^a$, $SO_2NR^aR^b$, $S(=O)R^a$, $S(=O)NR^aR^b$, $C(=O)NR^aC_{1-6}$alkyleneOR$^a$, $C(=O)NR^aC_{1-6}$alkyleneHet, $C(=O)C_{1-6}$alkylenearyl, $C(=O)C_{1-6}$alkyleneheteroaryl, $C_{1-6}$alkylenearyl, $C_{1-6}$alkyleneheteroaryl, $C_{1-6}$alkyleneHet, $C_{1-6}$alkyleneC(=O)$C_{1-6}$alkylenearyl, $C_{1-6}$alkyleneC(=O)$C_{1-6}$ alkyleneheteroaryl, $C_{1-6}$alkyleneC(=O)Het, $C_{1-6}$alkyleneC(=O)NR$^a$R$^b$, $C_{1-6}$alkyleneOR$^a$, $C_{1-6}$alkyleneNR$^a$C(=O)R$^a$, $C_{1-6}$alkyleneOC$_{1-6}$alkyleneOR$^a$, $C_{1-6}$alkyleneNR$^a$R$^b$, $C_{1-6}$alkyleneC(=Q)OR$^a$, $C_{1-6}$alkyleneOC$_{1-6}$alkyleneC(=O)OR$^a$, $C_{1-6}$alkyleneC(=O)aryl, $C_{1-6}$alkyleneC(=O) heteroaryl, $C_{1-6}$alkyleneOC$_{1-6}$alkylenearyl, $C_{1-6}$alkyleneOC$_{1-6}$alkyleneheteroaryl, $C_{1-6}$alkyleneOC$_{1-6}$alkyleneHet, $C_{1-6}$alkyleneSR$^a$, $C_{1-6}$alkyleneSO$_2$R$^a$, $C_{1-6}$alkyleneS(=O)R$^a$; $C_{1-6}$alkyleneSO$_2$NR$^a$R$^b$, and $C_{1-6}$alkyleneNHSO$_2$R$^a$;
- each $R^4$, independently, is selected from the group consisting of halo, OH, CN, NO$_2$, CF$_3$, CF$_3$O, NR$^a$R$^b$, $C_{1-8}$alkyl, $C_{1-8}$alkoxy, $C_{1-8}$alkanoyl, $C_{1-8}$alkoxycarbonyl, $C_{1-8}$alkanoyloxy, aryl, heteroaryl, $C_{1-6}$alkylenearyl, and $C_{1-6}$alkyleneheteroaryl;
- each $R^5$, independently, is selected from the group consisting of halo, $C_{1-8}$alkyl, $C_{1-8}$alkoxy, and OH;
- m is 0, 1, 2, 3, 4, 5, 6, 7, or 8;
- n is 0, 1, 2, 3, 4, 5, or 6;
- p is 0, 1; or 2;
- bond a and bond b represented by - - - are each independently a single bond or a double bond;
- R$^a$ and R$^b$, independently, are selected from the group consisting of hydrogen, $C_{1-8}$alkyl, aryl, heteroaryl, arylC$_{1-3}$alkyl, heteroarylC$_{1-3}$alkyl, $C_{1-3}$alkylenearyl, $C_{1-3}$alkyleneheteroaryl, and Het;

or a pharmaceutically acceptable salt or solvate thereof.

2. The compound of claim 1 which is a compound of formula (II):

(II)

or a pharmaceutically acceptable salt or solvate thereof.

3. The compound of claim 1 which is a compound of formula (III):

(III)

or a pharmaceutically acceptable salt or solvate thereof.

4. The compound of claim 1 wherein bond b represented by - - - is a single bond.

5. The compound of claim 2 wherein bond b represented by - - - is a single bond.

6. The compound of claim 3 wherein bond b represented by - - - is a single bond.

7. The compound of claim 1 wherein bond b represented by - - - is a double bond.

8. The compound of claim 2 wherein bond b represented by - - - is a double bond.

9. The compound of claim 3 wherein bond b represented by - - - is a double bond.

10. The compound of claim 1 wherein $R^3$ is selected from the group consisting of hydrogen, $C_{1-8}$alkyl, $C_{1-6}$alkyleneOR$^a$, $C_{1-6}$alkyleneC(=O)OR$^a$, $C_{1-6}$alkyleneC(=O)NR$^a$R$^b$, $C(=O)R^a$, $C(=S)NR^aR^b$, and $C(=O)C_{1-6}$alkylenearyl.

11. The compound of claim 1 wherein $R^1$ is selected from the group consisting of hydrogen and benzyl.

12. The compound of claim 11 wherein $R^2$ and $R^4$ are hydrogen.

13. The compound of claim 1 wherein $R^3$ is selected from the group consisting of hydrogen, $C_{1-8}$alkyl, $C_{1-6}$alkylenearyl, $C_{1-6}$alkyleneOR$^a$, carboxylic acid, $C_{1-6}$alkyleneC(=O)OR$^a$, and $C_{1-6}$alkyleneC(=O)NR$^a$R$^b$.

14. The compound of claim 13 wherein $R^3$ is selected from the group consisting of hydrogen, methyl, $C_4$alkylene-O-phenyl, —CH$_2$COOEt, —CH$_2$COOH, and PhNHC(=O)CH$_2$—.

15. The compound of claim 1 wherein each $R^2$, independently, is $C_{1-4}$alkyl or OH.

16. The compound of claim 1 wherein each $R^2$, independently, is halo, $C_{1-4}$alkoxy, or OH.

17. The compound of claim 1 wherein $R^3$ is hydrogen, $C_{1-8}$alkyl, aryl, heteroaryl, $C(=O)R^a$, $C(=O)OR^a$, $C(=O)NR^aR^b$, $C(=O)SR^a$, $C(=S)NR^aR^b$, $SO_2R^a$, $SO_2NR^aR^b$, $S(=O)R^a$, $S(=O)NR^aR^b$, $C_{1-6}$alkylenearyl, $C_{1-6}$alkyleneheteroaryl, $C_{1-6}$alkyleneHet, $C_{1-6}$alkyleneC (=O)NR$^a$R$^b$, C$_{1-6}$alkyleneOR$^a$, C$_{1-6}$alkyleneNR$^a$C(=O)R$^a$, C$_{1-6}$alkyleneNR$^a$R$^b$, C$_{1-6}$alkyleneC(=O)OR$^a$, C$_{1-6}$alkyleneC(=O)Het, C$_{1-6}$alkyleneC(=O)aryl, C$_{1-6}$alkyleneC(=O)heteroaryl, C$_{1-6}$alkyleneOC$_{1-6}$alkylenearyl, C$_{1-6}$alkyleneOC$_{1-6}$alkyleneheteroaryl, C$_{1-6}$alkyleneOC$_{1-6}$alkyleneHet, C$_{1-6}$alkyleneSR$^a$, C$_{1-6}$alkyleneSO$_2$R$^a$, C$_{1-6}$alkyleneS(=O)R$^a$; C$_{1-6}$alkyleneSO$_2$NR$^a$R$^b$, or C$_{1-6}$alkyleneNHSO$_2$R$^a$.

18. The compound of claim 1 wherein R$^3$ is hydrogen, C$_{1-8}$alkyl, aryl, heteroaryl, SO$_2$R$^a$, C$_{1-6}$alkylenearyl, C$_{1-6}$alkyleneheteroaryl, C$_{1-6}$alkyleneHet, C$_{1-6}$alkyleneC(=O)C$_{1-6}$alkylenearyl, C$_{1-6}$alkyleneC(=O)C$_{1-6}$alkyleneheteroaryl, C$_{1-6}$alkyleneC(=O)Het, C$_{1-6}$alkyleneC(=O)NR$^a$R$^b$, C$_{1-6}$alkyleneOR$^a$, C$_{1-6}$alkyleneNR$^a$C(=O)R$^a$, C$_{1-6}$alkyleneOC$_{1-6}$alkyleneOR$^a$, C$_{1-6}$alkyleneNR$^a$R$^b$, C$_{1-6}$alkyleneC(=O)OR$^a$, or C$_{1-6}$alkyleneOC$_{1-6}$alkyleneC(=O)OR$^a$.

19. The compound of claim 1 wherein R$^3$ is hydrogen, methyl, 4-phenoxybutyl, carboxymethyl (—CH$_2$COOH), or PhNHC(=O)CH$_2$—.

20. The compound of claim 1 wherein each R$^4$, independently, is halo, OH, CN, NO$_2$, CF$_3$, CF$_3$O, NR$^a$R$^b$, aryl, or heteroaryl.

21. The compound of claim 1 wherein each R$^4$, independently, is halo, OH, CN, NO$_2$, CF$_3$, CF$_3$O, NR$^a$R$^b$, C$_{1-8}$alkyl, C$_{1-8}$alkoxy, C$_{1-8}$alkanoyl, C$_{1-8}$alkoxycarbonyl, or C$_{1-8}$alkanoyloxy.

22. The compound of claim 1 wherein each R$^5$, independently, is C$_{1-8}$alkyl or OH.

23. The compound of claim 1 wherein each R$^5$, independently, is halo, C$_{1-8}$alkoxy, or OH.

24. The compound of claim 1 wherein m is 1 or 2.

25. The compound of claim 1 wherein n is 1 or 2.

26. The compound of claim 1 wherein n is 0.

27. The compound of claim 1 wherein p is 1 or 2.

28. The compound of claim 1, which is:

10-benzyl-7,8,9,10,11,12-hexahydro-3H-azepino[4,5-b]pyrano[3,2-e]indole;

10-benzyl-7-methyl-7,8,9,10,11,12-hexahydro-3H-azepino[4,5-b]pyrano[3,2-e]indole;

2,3,7,8,9,10,11,12-octahydro-1H-azepino[4,5-b]pyrano[3,2-e]indole;

2,3,7,8,9,10,11,12-octahydro-7-methyl-1H-azepino[4,5-b]pyrano[3,2-e]indole;

10-benzyl-7-(4-phenoxybutyl)-7,8,9,10,11,12-hexahydro-3H-azepino[4,5-b]pyrano[3,2-e]indole;

7-(4-phenoxybutyl)-7,8,9,10,11,12-octahydro-1H-azepino[4,5-b]pyrano[3,2-e]indole;

ethyl(10-benzyl-3,8,9,10,11,12-hexahydro-7H-azepino[4,5-b]pyrano[3,2-e]indol-7-yl)acetate;

(10-benzyl-3,8,9,10,11,12-hexahydro-7H-azepino[4,5-b]pyrano[3,2-e]indol-7-yl)acetic acid;

2-(10-benzyl-3,8,9,10,11,12-hexahydro-7H-azepino[4,5-b]pyrano[3,2-e]indol-7-yl)-N-phenylacetamide; or 2-(1,2,3,8,9,10,11,12-octahydro-7H-azepino[4,5-b]pyrano[3,2-e]indol-7-yl)-N-phenylacetamide;

or a pharmaceutically acceptable salt or solvate thereof.

29. The compound of claim 1, which is:

3,3-dimethyl-7,8,9,10,11,12-hexahydro-3H-azepino[4,5-b]pyrano[3,2-e]indole;

10-benzyl-3,3-dimethyl-7,8,9,10,11,12-hexahydro-3H-azepino[4,5-b]pyrano[3,2-e]indole;

7-phenyl-2,3,7,8,9,10,11,12-octahydro-1H-azepino[4,5-b]pyrano[3,2-e]indole;

7-benzyl-2,3,7,8,9,10,11,12-octahydro-1H-azepino[4,5-b]pyrano[3,2-e]indole; or rac-cis-2,3,7,7a,8,9,10,11,12,12a-decahydro-1H-azepino[4,5-b]pyrano[3,2-e]indole;

or a pharmaceutically acceptable salt or solvate thereof.

30. A pharmaceutical composition comprising a compound of claim 1 and a pharmaceutically acceptable excipient.

31. A method for treating a disease, disorder, or condition wherein a 5-HT receptor is implicated and modulation of a 5-HT function is desired in a mammal comprising administering to the mammal a therapeutically effective amount of a compound of claim 1 that modulates the 5-HT receptor.

32. The method of claim 31 wherein the disease, disorder, or condition is anxiety, obesity, depression, or a stress related disease.

33. A method to treat obesity, depression, schizophrenia, schizophreniformn disorder, schizoaffective disorder, delusional disorder, a stress related disease, panic disorder, a phobia, obsessive compulsive disorder, post-traumatic-stress syndrome, immune system depression, a stress induced problem with the urinary, gastrointestinal or cardiovascular system, neurodegenerative disorders, autism, chemotherapy-induced vomiting, hypertension, migraine headaches, cluster headaches, sexual dysfunction in a mammal, addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance, diminished cognition, bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder, Huntington's disorder, Tardive Dyskinesia, oppositional defiant disorder, peripheral neuropathy, post-traumatic stress disorder, premenstrual dysphoric disorder, a psychotic disorder, mood disorder, depressive disorder, bipolar disorder, seasonal affective disorder, sleep disorder, developmental disorder, agitation disorder, selective serotonin reuptake inhibition, "poop out" syndrome, Tic disorder or Tourette's syndrome in a mammal comprising administering a therapeutically effective amount of a compound of claim 1 to the mammal.

* * * * *

UNITED STATES PATENT AND TRADEMARK OFFICE
CERTIFICATE OF CORRECTION

PATENT NO. : 6,503,899 B2
DATED : January 7, 2003
INVENTOR(S) : Jian-min Fu

It is certified that error appears in the above-identified patent and that said Letters Patent is hereby corrected as shown below:

Column 27,
Line 44, delete "(=Q)OR$^a$" and insert -- (=O)OR$^a$ --,
Line 61, delete ";" after "1" and insert -- , --, therefor.

Signed and Sealed this

Twenty-second Day of July, 2003

JAMES E. ROGAN
*Director of the United States Patent and Trademark Office*